United States Patent [19]

Shephard et al.

[11] 4,147,793
[45] Apr. 3, 1979

[54] FUNGICIDAL AZOLYL-SUBSTITUTED ARYL ARALKYLKETONE COMPOUNDS

[75] Inventors: Margaret C. Shephard; Paul A. Worthington, both of Maidenhead, England

[73] Assignee: Imperial Chemical Industries Limited, London, England

[21] Appl. No.: 820,629

[22] Filed: Jul. 29, 1977

[30] Foreign Application Priority Data

Jul. 29, 1976 [GB] United Kingdom .............. 31650/76
Dec. 24, 1976 [GB] United Kingdom .............. 54111/76
May 5, 1977 [GB] United Kingdom .............. 18863/77

[51] Int. Cl.² ............... A01N 9/22; A01N 21/00; C07D 233/60; C07D 249/08
[52] U.S. Cl. ................................ 424/269; 260/299; 260/308 R; 424/245; 424/273 R; 548/341
[58] Field of Search .............. 260/299, 308 R; 548/341; 424/269, 273, 245

[56] References Cited

U.S. PATENT DOCUMENTS

3,914,427  10/1975  Kramer et al. ...................... 424/273

FOREIGN PATENT DOCUMENTS

2431407  1/1976  Fed. Rep. of Germany ...... 260/308 R

Primary Examiner—Alton D. Rollins
Attorney, Agent, or Firm—Cushman, Darby & Cushman

[57] ABSTRACT

Fungicidal compounds of the formula:

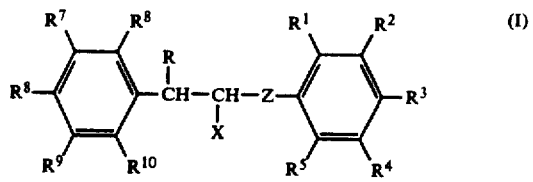

wherein R is alkyl, alkenyl or alkynyl having up to 6 (preferably up to 4) carbon atoms, substituted or unsubstituted aryl (e.g. phenyl), substituted or unsubstituted aralkyl (e.g benzyl), cyano, alkoxycarbonyl or trihalomethyl (e.g. trifluoromethyl), Z is C=O or a derivative thereof (e.g. a ketal, hydrazone, semicarbazone, oxime or imine), each of $R^1$ to $R^{10}$, which may be the same or different, is hydrogen, halogen, phenyl (particularly in the 4-position on the ring), $C_{1-4}$ alkyl, $C_{1-4}$ alkoxy, nitro or mono- or di-($C_{1-4}$ alkyl)-, aryl- or aralkyl-substituted or unsubstituted amino, at least four of $R^1$ to $R^{10}$ being hydrogen, and X is imidazol-1-yl, or 1, 2,4-triazol-1-yl, and acid addition salts and metal complexes of such compounds.

33 Claims, No Drawings

FUNGICIDAL AZOLYL-SUBSTITUTED ARYL ARALKYLKETONE COMPOUNDS

This invention relates to certain heterocyclic compounds which are imidazole or 1,2,4-triazole derivatives, to a process for preparing them, to fungicidal compositions containing them and to a method of combating fungal infections in plants using them.

The heterocyclic compounds have the formula (I):

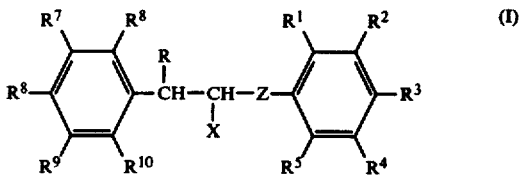

wherein R is alkyl, alkenyl or alkynyl having up to 6 (preferably up to 4) carbon atoms, substituted or unsubstituted aryl (e.g. phenyl), substituted or unsubstituted aralkyl (e.g. benzyl), cyano, alkoxycarbonyl [for example ($C_{1-4}$ alkoxy) carbonyl, e.g. methoxy- or ethoxy-carbonyl] or trihalomethyl (e.g. trifluoromethyl)], Z is C=O or a derivative thereof (e.g. a ketal, hydrazone, semicarbazone, oxime or imine), each of $R^1$ to $R^{10}$, which may be the same or different, is hydrogen, halogen, phenyl (particularly in the 4-position on the ring), $C_{1-4}$ alkyl, $C_{1-4}$ alkoxy, nitro or mono- or di-($C_{1-4}$ alkyl)-, aryl- or aralkyl-substituted or unsubstituted amino, at least four of $R^1$ to $R^{10}$ being hydrogen, and X is imidazol-1-yl or 1,2,4-triazol-1-yl, and acid addition salts and metal complexes of such compounds.

The compounds of the invention contain chiral centres. The compounds are generally obtained in the form of racemic mixtures. However, these or other mixtures can be separated into the individual isomers by methods known in the art.

The aryl groups and the aryl moieties of the aralkyl groups suitably have up to 10 carbon atoms; the alkyl moieties of the aralkyl groups suitably have up to 4 carbon atoms.

Suitable substituents on the aryl (e.g. phenyl) groups are halogen, alkyl [e.g. methyl, ethyl, propyl (n- or i-propyl) and butyl (n-, i- or t-butyl)], nitro, trifluoromethyl, cyano, phenyl, $C_{1-4}$ alkoxy (e.g. methoxy or ethoxy) or ($C_{1-4}$ alkylene)dioxy (e.g. methylenedioxy). The aryl and aralkyl groups suitably have one, two or three substituents. An example of a suitable substituted phenyl group is chlorophenyl (e.g. p-chlorophenyl). The aralkyl (e.g. benzyl) groups can be ring-substituted with the above groups or can be substituted in the alkyl moieties thereof with the groups mentioned above for the group R.

Examples of suitable alkyl, alkenyl, alkynyl and alkoxy groups are methyl, ethyl, propyl (n- or iso-propyl), butyl (n-, iso- or t-butyl), allyl, propynyl, methoxy, ethoxy, propoxy and butoxy.

The halogen can be fluorine, chlorine, bromine or iodine.

Preferably all of $R^1$ to $R^5$ and/or all of $R^6$ to $R^{10}$ are hydrogen or one or two of $R^1$ to $R^5$ and/or one or two of $R^6$ to $R^{10}$ are halogen, the rest being hydrogen. Especially preferred are those compounds wherein $R^3$, $R^6$ and/or $R^8$ are halogen (particularly fluorine, chlorine or bromine), the rest being hydrogen.

The compound of the invention is preferably one wherein R is alkyl, alkenyl or alkynyl having up to 4 carbon atoms, phenyl optionally substituted with one, two or three halogen, $C_{1-4}$ alkyl, nitro, trifluoromethyl, cyano, phenyl, $C_{1-4}$ alkoxy or ($C_{1-4}$ alkylene)dioxy, benzyl optionally ring-substituted with one, two or three halogen, $C_{1-4}$ alkyl, nitro, trifluoromethyl, cyano, phenyl, $C_{1-4}$ alkoxy or ($C_{1-4}$ alkylene)dioxy and/or substituted on the α-carbon atom with alkyl, alkenyl or alkynyl having up to 4 carbon atoms, phenyl, benzyl, cyano, ($C_{1-4}$ alkoxy)carbonyl or trihalomethyl, Z is C=O or a derivative thereof which is a ketal, hydrazone, semicarbazone, oxime or imine, each of $R^1$ to $R^{10}$, which may be the same or different, is hydrogen, halogen, phenyl, $C_{1-4}$ alkyl, $C_{1-4}$ alkoxy, nitro or mono- or di-($C_{1-4}$ alkyl)-, phenyl- or benzyl-substituted or unsubstituted amino, at least six of $R^1$ to $R^{10}$ being hydrogen, and X is imidazol-1-yl or 1,2,4-triazol-1-yl, or an acid addition salt or metal complex thereof. Especially preferred are those compounds wherein R is $C_{1-4}$ alkyl, pheny, chlorophenyl (e.g. 4-chlorophenyl) or cyano, Z is C=O, $R^1$, $R^2$, $R^4$, $R^5$, $R^7$, $R^9$, and $R^{10}$ are all hydrogen, each of $R^3$, $R^6$ and $R^8$, which may be the same or different, is hydrogen, fluorine, chlorine or bromine, and X is 1,2,4-triazol-1-yl, or an acid addition salt or metal complex thereof.

Suitable acid addition salts are salts with inorganic or organic acids, e.g. hydrochloric, nitric, sulphuric, acetic or oxalic acid.

The metal complex is suitably one including copper, zinc, manganese or iron. It preferably has the formula:

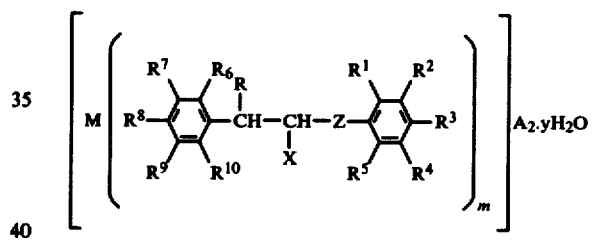

wherein R, Z, $R^1$ to $R^{10}$ and X are as defined above, M is a metal, A is an anion (e.g. a chloride, bromide, iodide, nitrate, sulphate or phosphate anion), m is 2 or 4 and y is 0 or an integer of 1 to 12.

Specific examples of the compounds are given in Table I wherein $R^1$, $R^2$, $R^4$, $R^5$, $R^7$, $R^9$ and $R^{10}$ are all hydrogen, Z is C=O and X is 1,2,4-triazol-1-yl (Compounds 1 to 45) or imidazol-1-yl (Compounds 46 to 57).

TABLE I

| COMPOUND NO | R | $R^3$ | $R^6$ | $R^8$ | MELTING POINT (° C.) |
|---|---|---|---|---|---|
| 1 | Me | H | H | H | 166°–168° |
| 2 | Me | Cl | H | H | 163°–165° |
| 3 | Me | Cl | H | Cl | 163°–165° |
| 4 | Me | Cl | H | F | 151°–153° |
| 5 | Et | Cl | H | H | 125°–126° |
| 6 | n-Bu | Cl | H | H | oil |
| 7 | n-Pr | Cl | H | H | 102°–104° |
| 8 | $C_6H_5$ | Cl | H | H | 157°–159° |
| 9 | p-Cl-$C_6H_4$ | Cl | H | Cl | 174°–176° |
| 10 | $C_6H_5$ | H | H | H | 168°–170° |
| 11 | p-Cl-$C_6H_4$ | H | H | H | 192°–194° |
| 12 | Me | F | H | H | 152°–156° |
| 13* | Me | F | H | F | oil |
| 14* | Me | F | H | F | 123°–125° |
| 15 | Et | F | H | H | 80°–83° |
| 16* | n-Bu | F | H | H | oil |
| 17 | Me | F | H | Cl | 109°–111° |
| 18* | Me | F | H | F | 128°–129° |

TABLE I-continued

| COMPOUND NO | R | R³ | R⁶ | R⁸ | MELTING POINT (° C.) |
|---|---|---|---|---|---|
| 19ˣ | n-Pr | F | H | H | 60°-64° |
| 20° | Et | F | H | Cl | 123°-125° |
| 21° | Et | F | H | Cl | 115°-117° |
| 22 | Me | Cl | H | Br | 138°-141° |
| 23 | n-Pr | F | H | Cl | 112°-115° |
| 24 | n-Bu | F | H | Cl | |
| 25 | Me | H | H | Cl | 126°-128° |
| 26 | Me | F | H | Br | |
| 27 | Me | H | H | Br | 115°-118° |
| 28 | CN | Cl | H | Cl | |
| 29 | CN | H | H | Cl | |
| 30 | CN | F | H | Cl | |
| 31+ | Me | H | Cl | Cl | 150°-151° |
| 32+ | Me | Cl | Cl | Cl | 129°-131° |
| 33+ | Me | F | Cl | Cl | 135°-138° |
| 34 | Et | H | H | F | |
| 35 | Et | F | H | F | |
| 36 | Et | Cl | H | F | 125°-126° |
| 37 | n-Pr | H | H | F | |
| 38 | n-Pr | Cl | H | F | |
| 39 | n-Pr | F | H | F | |
| 40+ | Me | Br | H | Cl | 174°-175° |
| 41+ | Me | H | H | F | 148°-149° |
| 42+ | Et | Cl | H | F | oil |
| 43+ | n-Bu | F | H | F | 102°-105° |
| 44 | Me | H | F | H | 155°-157° |
| 45 | Me | Cl | F | H | 162°-164° |
| 46 | Me | H | H | H | |
| 47 | Me | H | H | Cl | |
| 48 | Me | H | H | F | |
| 49 | Me | Cl | H | H | |
| 50 | Me | Cl | H | Cl | |
| 51 | Me | Cl | H | F | |
| 52 | Et | Cl | H | H | |
| 53 | Et | Cl | H | Cl | 193°-195° |
| 54 | Et | Cl | H | F | |
| 55 | Me | F | H | H | |
| 56 | Me | F | H | Cl | |
| 57 | Me | F | H | F | |

*Compounds 14 and 18 are diastereoisomers of each other; Compound 13 is a mixture of these diastereoisomers.
ˣThese compounds are mixtures of diastereoisomers.
°These compounds are diastereoisomers of each other.
+These compounds are single diastereoisomers.

The compounds may be made by reacting imidazole or 1,2,4-triazole or a salt thereof with the appropriate α-halo ketone by any of the methods set out in the literature. Thus for example 1,2,4-triazole can be reacted with a α-halo ketone of formula (II):

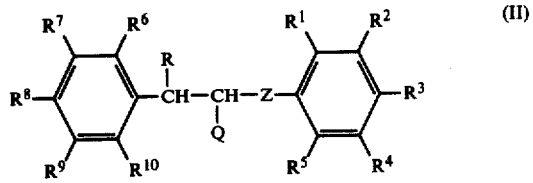

(II)

wherein Q is halogen (preferably bromine or chlorine) and R, R¹ to R¹⁰ and Z are as defined above.

This process may in some cases be carried out by merely heating the reactants together in the absence of a solvent or diluent, but preferably a solvent is present. Suitable solvents are non-hydroxylic solvents such as acetonitrile (which is preferred), dimethylformamide, dimethyl sulphoxide, sulpholane and tetrahydrofuran. Hydroxylated solvents (e.g. methanol and ethanol) may be used in certain circumstances when the presence of the hydroxyl group does not interfere with the progress of the reaction.

The process may also be carried out in the presence of a base, but preferably excess imidazole or triazole is present to remove liberated HX from the reaction. Other suitable bases include sodium hydride (although not when a hydroxylated solvent or diluent is used), alkali metal carbonates (such as potassium carbonate) and alkali metal hydroxides (such as potassium hydroxide). The temperature at which the reaction may be carried out will depend upon the choice of reactants, solvent and base, but generally the reaction mixture is heated under reflux.

The process generally involves dissolving the reactants in a solvent and, after allowing reaction to occur, isolating the product by removal of the solvent in vacuo. Unreacted imidazole or triazole can be removed by extraction with a suitable solvent which is then washed with water. Crystallisation or other purification procedures (e.g. chromatography) may then be carried out, if desired. Chromatography is a suitable means for separating the diastereoisomers.

The α-haloketone starting material may be made by any of the methods set out in the literature.

The compounds may also be made by aralkylating the corresponding compound of formula (III):

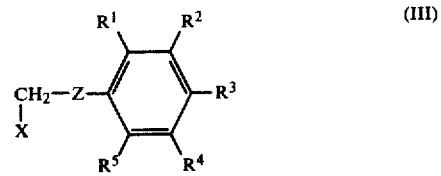

(III)

wherein Z, X and R¹ to R⁵ are as defined above, e.g. by first reacting it with an alkali metal hydride (e.g. sodium hydride) in a convenient solvent (such as dimethylformamide or tetrahydrofuran) to produce the alkali metal salt which is reacted with for example an α-(alkyl- or phenyl-) aralkyl halide e.g. a bromide (which is preferred) or a chloride.

This process generally involves dissolving the compound of formula (III) in the solvent and adding an equivalent amount of the alkali metal hydride, and then, after allowing the reaction to occur, the aralkyl halide is added dropwise. After the reaction, the product can be isolated by pouring into water and recrystallising the solid formed from a convenient solvent, or purifying the resultant oil by column chromatography or another convenient technique.

The acid addition salts and metal complexes of the compounds of formula (I) can be prepared in known manner. For example, the complexes can be prepared by reacting the uncomplexed compound with a metal salt in a suitable solvent.

The compounds are active fungicides, particularly against the diseases:

*Piricularia oryzae* on rice

*Puccinia recondita, Puccinia striiformis* and other rusts on wheat, *Puccinia hordei, Puccinia striiformis* and other rusts on barely, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Cercospora arachidicola* on peanuts and other Cercospora species on for example sugar beet, bananas and soyabeans

*Botrytis cinerea* (grey mould) on tomatoes, strawberries, vines and other hosts

*Phytophthora infestans* (blight) on tomatoes

*Venturia inaequalis* (scab) on apples.

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: Fusarium spp., Septoria spp., Tilletia spp. (i.e. bunt, a seed borne disease of wheat), Ustilago spp., and Pyrenophora spp. on cereals. Some compounds have also shown activity against *Rhizoctonia solani*, an important disease of cotton and rice.

The compounds also have certain plant growth regulating activities (particularly a stunting effect on the vegetative growth of mono- and di-cotyledonous plants), and antibacterial activities (e.g. against *Erwinia amylovora*) and antiviral activities (e.g. against tobacco mosaic virus) as well as herbicidal and algicidal activity.

The compounds may be used as such for fungicidal purposes but are more conveniently formulated into compositions for such usage. The invention thus provides also a fungicidal composition comprising a compound of general formula (I) or a salt or complex thereof as hereinbefore defined and a carrier or diluent.

The invention also provides a method of combating fungal diseases in a plant, which method comprises applying to the plant, to seed of the plant or to the locus of the plant or seed a compound or salt or complex thereof as hereinbefore defined.

The compounds can be used to combat plant fungi and treat plants or seeds in a number of ways, for example they can be applied, formulated or unformulated, directly to the foliage of a plant which is infected or likely to become infected, or they can be applied also to bushes and trees, to seeds or to other medium in which plants, bushes or trees are growing or are to be planted, or they can be sprayed on, dusted on or applied as a cream or paste formulation. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes and trichloroethylene.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The compounds can be used as mixtures with fertilisers (e.g. nitrogen—or phosphorus—containing fertilisers). Compositions comprising only granules of fertiliser incorporating, for example coated with, the compound, are preferred. The invention therefore also provides a fertiliser composition comprising the compound of general formula (I) or a salt or complex thereof as hereinbefore defined.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-anionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity (e.g. growth stimulating substances such as the gibberellins and other compounds having complementary fungicidal or insecticidal activity), as well as stabilising agent(s), for example epoxides (e.g. epichlorhydrin). The other fungicidal compound can be one which is capable of combating ear diseases of cereals (e.g. wheat) such as Septoria, Gibberella, Helminthosporium and the sooty mould complex.

The following Examples illustrate the invention; the temperatures are given in degrees Centigrade (° C.).

EXAMPLE 1

2-(1,2,4-Triazol-1-yl)-3-phenylbutyrophenone (Compound 1)

Stage 1: Bromine (0.02 mol) was added dropwise to a stirred solution of 2-(α-methylbenzyl)acetophenone (0.02 mol) in dry diethyl ether (20 ml) at 5° over one hour. The ether was removed in vacuo and the residue redissolved in ether (100 ml), washed with saturated sodium bicarbonate solution (2 × 100 ml) and then water (4 × 100 ml), and dried over anhydrous sodium sulphate. Removal of the solvent gave a solid which on recrystallisation from petroleum ether (40°–60°) gave 2-bromo-3-phenylbutyrophenone, m.p. 69°–71°.

Stage 2: 2-Bromo-3-phenyl-butyrophenone (0.02 mol), 1,2,4-triazole (0.02 mol) and potassium carbonate (0.04 mol) were refluxed in methyl ethyl ketone (100 ml) for 36 hours. After cooling to room temperature, the solution was filtered and the solvent removed in vacuo. Recrystallisation of the residue from ethanol/petroleum ether (60°–80°) gave the title compound as a colourless solid, m.p. 166°–8°.

Analysis $C_{18}H_{17}ON_3$ requires %C, 74.2; %H, 5.8; %N, 14.4. found %C, 74.4; %H, 6.1; %N, 14.5.

EXAMPLE 2

2-(1,2,4-Triazol-1-yl)-3-phenyl-4'-chlorobutyrophenone (Compound 2)

Stage 1: 2,4'-Dichloroacetophenone (0.03 mol) and 1,2,4-triazole (0.03 mol) were suspended in acetonitrile (50 ml) and cooled to −20°. Triethylamine (0.03 mol) was added dropwise with stirring. After stirring at −20° for 2 hours, the mixture was poured into water, and the product filtered off, washed with water, dried and crystallised from toluene to give pale yellow needles of 2-(1,2,4-triazol-1-yl)-4'-chloroacetophenone, m.p. 151°–3°.

$C_{10}H_8ON_3Cl$ requires %C, 54.2; %H, 3.6; %N, 19.0. found %C, 54.2; %H, 3.7; %N, 19.1.

Stage 2: 2-(1,2,4-Triazol-1-yl)-4'-chloroacetophenone (0.01 mol) was dissolved in dimethylformamide (5.0 ml) at room temperature and treated with sodium hydride (0.01 mol). When the reaction was complete (3 hours), the mixture was cooled to 0° and α-methylbenzyl chloride (0.01 mol) was added dropwise with stirring. After stirring at room temperature for 20 hours, the mixture was poured into water and the product filtered off. Recrystallisation from chloroform/petroleum ether (60°–80°) gave the title compound as a colourless crystalline solid, m.p. 163°–5°.

$C_{18}H_{16}ON_3Cl$ requires %C, 66.4; %H, 4.9; %N, 12.9. found %C, 66.5; %H, 4.9; %N, 13.0.

EXAMPLE 3

This Example illustrates two of the compositions of the invention.

(1) Emulsifiable Concentrate
Compound 13—200 g/kg
Arylan SBC acid—100 g/kg
Arylan PWS—200 g/kg
Dimethylformamide—to 1 kg (2) Powder useful as Seed Dressing
Compound 14—250 g/kg
Dodecylbenzene—30 g/kg
Talc 52—to 1 kg

EXAMPLE 4

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the foliage diseases, 100 p.p.m. a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and to the foliage (by spraying) one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 14 days according to the disease and environment.

The disease control was recorded by the following grading:
4 = No disease
3 = 0–5%
2 = 6–25%
1 = 26–60%
0 = > 60%

The results are shown in Table II.

TABLE II

| | DISEASE CONTROL | | | | | | |
|---|---|---|---|---|---|---|---|
| COMPOUND NO | Puccinia recondita in wheat | Phytophthora infestans in tomato | Plasmopara viticola in vines | Piricularia oryzae in rice | Cercospora arachidicola on peanuts | Botrytis cinerea in tomato | Erysiphe graminis in barley |
| 1 | 4 | 0 | 2 | 0 | | 2 | 4 |
| 2 | 3–4 | 0* | 0 | 0–1 | | 0–1 | 4 |
| 3 | 3–4 | 0 | 0 | 0–2* | | 0 | 4 |
| 4 | 3* | 2–3 | 0 | 1–3 | | 3 | 4 |

TABLE II-continued

| COMPOUND NO | DISEASE CONTROL | | | | | | |
|---|---|---|---|---|---|---|---|
| | Puccinia recondita in wheat | Phytophthora infestans in tomato | Plasmopara viticola in vines | Piricularia oryzae in rice | Cercospora arachidicola on peanuts | Botrytis cinerea in tomato | Erysiphe graminis in barley |
| 5 | 3 | 0 | 0 | 1 | | 3-4 | 4 |
| 6 | 3 | 0 | 0 | 0-2 | | 2 | 4 |
| 7 | 3 | 0 | 0 | 2-3 | | 2 | 4 |
| 8 | 3-4 | 0 | 0 | 1-2 | | | 4 |
| 9 | 3 | 0 | 0 | 0 | | 3 | 3 |
| 10 | 3-4 | 0 | 0 | 0 | | 0 | 4 |
| 11 | 1-2 | 0 | 0 | 0-1 | | 2 | 3-4 |
| 12 | 4 | 0 | 0 | 1-2 | | 1-2 | 4 |
| 13 | 4 | 1-2 | 0 | 0-2 | | 0 | 3-4 |
| 14 | 4 | 0-1 | 0 | 1-3 | | 3 | 4 |
| 15 | 3-4 | 0 | 0 | 1-2 | | 3 | 4 |
| 16 | 3-4 | 0 | 3-4 | 0 | 0-1 | 1-2 | 4 |
| 17 | 4 | | | 2-3 | | 1 | 4 |
| 18 | 3-4 | 0 | 0 | 0 | 2-3 | 3-4 | 4 |
| 19 | 4 | 0 | 0-3 | 0 | 2 | 3 | 4 |
| 20 | 4 | 0 | 3 | 0-1 | 3 | 3 | 4 |
| 21 | 4 | 1 | 0 | 0 | 3 | 0 | 4 |
| 22 | 3 | 0 | 0 | 0 | 3 | 0 | 4 |
| 23 | | 0 | 2 | 1 | | 3 | |
| 24 | | | | | | | |
| 25 | 4 | 1 | 0 | 0 | 2 | 3 | 4 |
| 26 | | | | | | | |
| 27 | 4 | 1 | 2 | 0 | 1 | 2 | 3 |
| 28 | | | | | | | |
| 29 | | | | | | | |
| 30 | | | | | | | |
| 31 | | 0 | 0 | 1 | | 2 | |
| 32 | | | | | | | |
| 33 | | 0 | 0 | 3 | | 3 | |
| 34 | | | | | | | |
| 35 | | | | | | | |
| 36 | | | | | | | |
| 37 | | | | | | | |
| 38 | | | | | | | |
| 39 | | | | | | | |
| 40 | 2 | 0 | 0 | 0 | 0 | 0 | 4 |

*Test at 50 p.p.m.

EXAMPLE 5

This Example illustrates the protectant activity (at 50 ppm) of the compounds against various fruit fungal diseases.

The activity of the compounds against apple powdery mildew (*Podosphaera leucotricha*) and vine powdery mildew (*Uncinula necator*) was determined as follows.

Small apple (Jonathan) and vine plants about 3 weeks old and growing in mini pots (diameter: 3 cm) were sprayed first with the solution or suspension of the test compound, allowed to dry overnight in a growth room and then infected on the following day with spores of the disease by placing them in an enclosed space and allowing spores of the disease blown into the still space to settle upon them over four to six hours.

Assessment was made of the percentage amount of disease on the leaves of the plants (after 8 days for apples and 9 to 10 days for vines).

The tests against apple scab (*Venturia inaequalis*) were performed as follows.

*Venturia inaequalis* was treated as an obliqate parasite, the spores of the fungus being transferred from plant to plant by-passing agar plate culture which ensures a very pathogenic fungus.

Infected leaves were removed from stock plants 13 days after inoculation. The spores were removed from the leaves by agitation in a small volume of deionised water, counted and then adjusted to 100,000 spores/ml. This suspension was sprayed onto the undersides of clean apple seedling leaves of three equally susceptible varieties, i.e. Jonathan, Granny Smith and Red Delicious. The infected seedlings were immediately placed in a high humidity cabinet at 19° C. and left therein for 48 hours. After this incubation period the plants were placed in growth room conducive to disease development. The disease was easily assessed 12 or 13 days after inoculation.

The test compound was applied 24 hours after inoculation.

The grading system used is the same as for the cereal fungicide tests. Table III shows the results.

TABLE III

| COMPOUND NO | DISEASE CONTROL | | |
|---|---|---|---|
| | Podosphaera leucotricha on apples | Uncinula necator on vines | Venturia inaequalis on apples |
| 1 | 0 | 1-2 | 0 |
| 2 | 1 | 2 | 0 |
| 3 | 1 | 4 | 1 |
| 4 | 2 | 4 | 2 |
| 5 | 3 | 4 | 0-2 |
| 6 | 4 | 4 | 2 |
| 7 | 2 | 4 | 1 |
| 8 | 1 | 4 | 1 |
| 9 | 0 | 1 | |
| 10 | 0 | 4 | |
| 11 | 0 | 1 | 0 |
| 12 | 2 | 4 | 4 |
| 13 | 4 | 4 | 4 |
| 14 | 4 | 4 | 4 |
| 15 | 1 | 4 | 0 |
| 16 | 4 | 4 | 2 |
| 17 | 4 | 4 | 3 |
| 18 | 2 | 1 | 2 |
| 19 | 4 | 4 | 2 |

TABLE III-continued

| COMPOUND NO | DISEASE CONTROL | | |
|---|---|---|---|
| | Podosphaera leuchotricha on apples | Uncinula necator on vines | Venturia inaequalis on apples |
| 20 | 4 | 4 | 4 |
| 21 | 4 | 4 | 4 |
| 22 | 0 | 4 | 1 |
| 23 | 4 | 4 | 3 |
| 24 | | | |
| 25 | 1 | 4 | 2 |
| 26 | | | |
| 27 | 2 | 4 | 1 |
| 28 | | | |
| 29 | | | |
| 30 | | | |
| 31 | | | |
| 32 | | | |
| 33 | | | |
| 34 | | | |
| 35 | | | |
| 36 | | | |
| 37 | | | |
| 38 | | | |
| 39 | | | |
| 40 | 0 | 2 | 0 |

We claim:

1. A compound of formula (I):

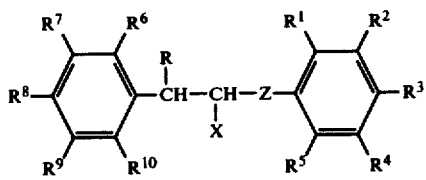

wherein R is alkyl, alkenyl or alkynyl having up to 4 carbon atoms, phenyl optionally substituted with one, two or three halogen, $C_{1-4}$ alkyl, nitro, trifluoromethyl, cyano, phenyl, $C_{1-4}$ alkoxy or ($C_{1-4}$ alkylene)dioxy, benzyl optionally ring-substituted with one, two or three halogen, $C_{1-4}$ alkyl, nitro, trifluoromethyl, cyano, phenyl, $C_{1-4}$ alkoxy or ($C_{1-4}$ alkylene)dioxy and/or substituted on the α-carbon atom with alkyl, alkenyl or alkynyl having up to 4 carbon atoms, phenyl, benzyl, cyano, ($C_{1-4}$ alkoxy)carbonyl or trihalomethyl, Z is C=O, each of $R^1$ to $R^{10}$, which may be the same or different, is hydrogen, halogen, phenyl, $C_{1-4}$ alkyl, $C_{1-4}$ alkoxy, nitro or mono- or di-($C_{1-4}$ alkyl)-, phenyl- or benzyl-substituted or unsubstituted amino, at least six of $R^1$ to $R^{10}$ being hydrogen, and X is 1,2,4-triazol-1-yl, or an acid addition salt or metal complex thereof.

2. A compound as claimed in claim 1 wherein R is $C_{1-4}$ alkyl, phenyl, chlorophenyl or cyano, Z is C=O, $R^1$, $R^2$, $R^4$, $R^5$, $R^7$, $R^9$ and $R^{10}$ are all hydrogen, each of $R^3$, $R^6$ and $R^8$, which may be the same or different, is hydrogen, fluorine, chlorine or bromine, and X is 1,2,4-triazol-1-yl, or an acid addition salt or metal complex thereof.

3. A compound as claimed in claim 1 which is 2-(1,2,4-triazol-1-yl)-3-(p-fluorophenyl)-4'-chlorobutyrophenone.

4. A compound as claimed in claim 1 which is 2-(1,2,4-triazol-1-yl)-3-phenyl-4'-chlorovalerophenone.

5. A compound as claimed in claim 1 which is 2-(1,2,4-triazol-1-yl)-3-phenyl-4'-chloroheptaphenone.

6. A compound as claimed in claim 1 which is 2-(1,2,4-triazol-1-yl)-3-phenyl-4'-chlorohexaphenone.

7. A compound as claimed in claim 1 which is 2-(1,2,4-triazol-1-yl)-3-phenyl-4'-fluorobutyrophenone.

8. A compound as claimed in claim 1 which is 2-(1,2,4-triazol-1-yl)-3-(p-fluorophenyl)-4'-fluorobutyrophenone.

9. A fungicidal composition consisting essentially of, as active ingredient, a fungicidally effective amount of a compound, salt or complex as claimed in claim 1, and a carrier for the active ingredient.

10. A fungicidal composition consisting essentially of, as active ingredient, a fungicidally effective amount of a compound, salt or complex as claimed in claim 2, and a carrier for the active ingredient.

11. A fungicidal composition consisting essentially of, as active ingredient, a fungicidally effective amount of a compound as claimed in claim 3, and a carrier for the active ingredient.

12. A fungicidal composition consisting essentially of, as active ingredient, a fungicidally effective amount of a compound as claimed in claim 4, and a carrier for the active ingredient.

13. A fungicidal composition consisting essentially of, as active ingredient, a fungicidally effective amount of a compound as claimed in claim 5, and a carrier for the active ingredient.

14. A fungicidal composition consisting essentially of, as active ingredient, a fungicidally effective amount of a compound as claimed in claim 6, and a carrier for the active ingredient.

15. A fungicidal composition consisting essentially of, as active ingredient, a fungicidally effective amount of a compound as claimed in claim 7, and a carrier for the active ingredient.

16. A fungicidal composition consisting essentially of, as active ingredient, a fungicidally effective amount of a compound as claimed in claim 8, and a carrier for the active ingredient.

17. A method of combating fungal diseases in a plant, the method consisting essentially of the step of applying to the plant, to seed of the plant or to the locus of the plant or seed, a fungicidally effective amount of a compound, salt or complex as claimed in claim 1.

18. A method of combating fungal diseases in a plant, the method consisting essentially of the step of applying to the plant, to seed of the plant or to the locus of the plant or seed, a fungicidally effective amount of a compound, salt or complex as claimed in claim 2.

19. A method of combating fungal diseases in a plant, the method consisting essentially of the step of applying to the plant, to seed of the plant or to the locus of the plant or seed, a fungicidally effective amount of a compound as claimed in claim 3.

20. A method of combating fungal diseases in a plant, the method consisting essentially of the step of applying to the plant, to seed of the plant or to the locus of the plant or seed, a fungicidally effective amount of a compound as claimed in claim 4.

21. A method of combating fungal diseases in a plant, the method consisting essentially of the step of applying to the plant, to seed of the plant or to the locus of the plant or seed, a fungicidally effective amount of a compound as claimed in claim 5.

22. A method of combating fungal diseases in a plant, the method consisting essentially of the step of applying to the plant, to seed of the plant or to the locus of the plant or seed, a fungicidally effective amount of a compound as claimed in claim 6.

23. A method of combating fungal diseases in a plant, the method consisting essentially of the step of applying to the plant, to seed of the plant or to the locus of the plant or seed, a fungicidally effective amount of a compound as claimed in claim 7.

24. A method of combating fungal diseases in a plant, the method consisting essentially of the step of applying to the plant, to seed of the plant or to the locus of the plant or seed, a fungicidally effective amount of a compound as claimed in claim 8.

25. A method of combating a fungal disease in a plant, said fungal disease caused by Venturia species, the method consisting essentially of the step of applying to the plant, to seed of the plant or to the locus of the plant or seed, a fungicidally effective amount of a compound of formula (I):

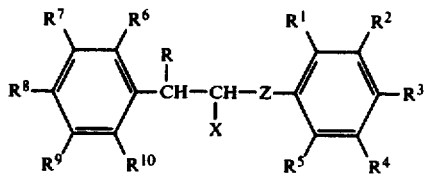

wherein R is alkyl, alkenyl or alkynyl having up to 4 carbon atoms, phenyl optionally substituted with one, two or three halogen, $C_{1-4}$ alkyl, nitro, trifluoromethyl, cyano, phenyl, $C_{1-4}$ alkoxy or ($C_{1-4}$ alkylene)dioxy, benzyl optionally ring-substituted with one, two or three halogen, $C_{1-4}$ alkyl, nitro, trifluoromethyl, cyano, phenyl, $C_{1-4}$ alkoxy or ($C_{1-4}$ alkylene)dioxy or substituted on the α-carbon atom with alkyl, alkenyl or alkynyl having up to 4 carbon atoms, phenyl, benzyl, cyano, ($C_{1-4}$ alkoxy)carbonyl or trihalomethyl, Z is C=O, each of $R^1$ to $R^{10}$, which may be the same or different, is hydrogen, halogen, phenyl, $C_{1-4}$ alkyl, $C_{1-4}$ alkoxy, nitro or mono- or di-($C_{1-4}$ alkyl)-, phenyl- or benzyl-substituted or unsubstituted amino, at least six of $R^1$ to $R^{10}$ being hydrogen, and X is 1,2,4-triazol-1-yl, or an acid addition salt or metal complex thereof.

26. A method as claimed in claim 25 wherein the Venturia species is *Venturia inaequalis* and the plant is an apple tree.

27. A method as claimed in claim 25 wherein, in the compound, R is $C_{1-4}$ alkyl, phenyl, chlorophenyl or cyano, $R^1$, $R^2$, $R^4$, $R^5$, $R^7$, $R^9$ and $R^{10}$ are all hydrogen, each of $R^3$, $R^6$ and $R^8$, which may be the same or different, is hydrogen, fluorine, chlorine or bromine, and X is 1,2,4-triazol-1-yl, or an acid addition salt or metal complex thereof.

28. A method as claimed in claim 25 wherein the compound is 2-(1,2,4-triazol-1-yl)-3-(p-fluorophenyl)-4'-chlorobutyrophenone.

29. A method as claimed in claim 25 wherein the compound is 2-(1,2,4-triazol-1-yl)-3-phenyl-4'-chlorovalerophenone.

30. A method as claimed in claim 25 wherein the compound is 2-(1,2,4-triazol-1-yl)-3-phenyl-4'-chloroheptaphenone.

31. A method as claimed in claim 25 wherein the compound is 2-(1,2,4-triazol-1-yl)-3-phenyl-4'-chlorohexaphenone.

32. A method as claimed in claim 25 wherein the compound is 2-(1,2,4-triazol-1-yl)-3-phenyl-4'-fluorobutyrophenone.

33. A method as claimed in claimed in claim 25 wherein the compound is 2-(1,2,4-triazol-1-yl)-3-(p-fluorophenyl)-4'-fluorobutyrophenone.

* * * * *